(12) United States Patent
Nobles, Jr. et al.

(10) Patent No.: US 7,803,601 B2
(45) Date of Patent: *Sep. 28, 2010

(54) PRODUCTION AND SECRETION OF GLUCOSE IN PHOTOSYNTHETIC PROKARYOTES (CYANOBACTERIA)

(75) Inventors: David R. Nobles, Jr., Austin, TX (US); R. Malcolm Brown, Jr., Austin, TX (US)

(73) Assignee: Board of Regents, The University of Texas, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/866,872

(22) Filed: Oct. 3, 2007

(65) Prior Publication Data

US 2008/0085520 A1     Apr. 10, 2008

Related U.S. Application Data

(60) Provisional application No. 60/849,363, filed on Oct. 4, 2006.

(51) Int. Cl.
| | |
|---|---|
| C12N 1/20 | (2006.01) |
| C12N 1/12 | (2006.01) |
| C12N 15/00 | (2006.01) |
| C12N 9/10 | (2006.01) |
| C12P 19/04 | (2006.01) |
| C12P 19/02 | (2006.01) |
| C12Q 1/68 | (2006.01) |

(52) U.S. Cl. .............. 435/252.3; 435/257.2; 435/320.1; 435/6; 435/15; 435/18; 435/100; 435/101; 435/105; 435/193

(58) Field of Classification Search .................. None
See application file for complete search history.

(56) References Cited

U.S. PATENT DOCUMENTS

| | | | |
|---|---|---|---|
| 4,224,410 | A | 9/1980 | Pemberton et al. |
| 4,310,629 | A | 1/1982 | Muller et al. |
| 4,560,659 | A | 12/1985 | Asturias |
| 4,840,902 | A | 6/1989 | Lawford |
| 6,541,238 | B1 * | 4/2003 | Saxena et al. ............ 435/252.3 |
| 6,699,696 | B2 | 3/2004 | Woods et al. |
| 2002/0102699 | A1 | 8/2002 | Wicher et al. |
| 2003/0104522 | A1 | 6/2003 | Ding et al. |

OTHER PUBLICATIONS

Moreno et al., Outdoor cultivation of a nitrogen-fixing marine cyanobacterium, *Anabena* sp. ATTC 33047. Biomol. Eng., 2003, vol. 20: 191-197.*

Yagashita et al., Effects of glucose addition and light on current outputs in Photosynthetic electrochemical cells using *Synechocystis* sp. PCC6714. J. Biosci. Bioeng., 1999, vol. 88 (2): 210-214.*

Kisand et al., Bacterioplankton strategies for leucine and glucose uptake after a cyanobacterial boom in an eutrophic shallow lake. Soil & Biochemistry, 2000, vol. 32: 1965-1972.*

Broun et al., Catalytic plasticity of fatty acid modification enzymes underlying chemical diversity of plant lipids. Science, 1998, vol. 282: 1315-1317.*

Kisselev L., Polypeptide release factors in prokaryotes and eukaryotes: same function, different structure. Structure, 2002, vol. 10: 8-9.*

Seffernick et al., Melamine deaminase and Atrazine chlorohydrolase: 98 percent identical but functionally different. J. Bacteriol.,2001, vol. 183 (8): 2405-2410.*

Wishart et al., A single mutation converts a novel phosphotyrosine binding domain into a dual-specificity phosphatase. J. Biol. Chem., 1995, vol. 270(45): 26782-26785.*

Wong et al., Genetic organization of the cellulose synthase operon in *Acetobacter xylinum*. Proc, Natl. Acad. Sci., 1990, vol. 87 (20): 813-8134.*

Witkowski et al., Conversion of b-ketoacyl synthase to a Malonyl Decarboxylase by replacement of the active cysteine with glutamine. Biochemistry, 1999, vol. 38: 11643-11650.*

Devos et al., Practical limits of function prediction. Proteins: Structure, Function, and Genetics. 2000, vol. 41: 98-107.*

Andersson, C.A., et al., "Application of bioluminescence to the study of circadian rhythms in cyanobacteria." In Zielger MM and Goldwin TO (eds) Methods in Enzymology (2000), vol. 305 pp. 527-542. Academic Press, Inc. New York.

Asada, T., et al., "Heterologous expression of clostridial hydrogenase in the cyanobacterium *Synechococcus* PCC 7942." Biochim Biophys Acta. (2000), 1490:269-278.

Bajpai, P., "Biological bleaching of chemical pulps." Crit Rev Biotechnol. (2004), 24(1):1-58.

Brown, Jr., R.M. "Position paper: microbial cellulose a new resource for wood, paper, textiles, food and specialty products," (2004), visit: <www.botany.utexas.edu/facstaff/facpages/mbrown/position1.htm>.

Cogne, G., et al., "Design, operation, and modeling of a membrane photobioreactor to study the growth of the Cyanobacterium *Arthrospira platensis* in space conditions." Biotechnol Prog. (2005), 21(3):741-50.

Czaja, W., et al., "Microbial cellulose—the natural power to heal wounds." Biomaterials. (2006), 27:145-151.

Deng, M.D., et al., "Ethanol synthesis by genetic engineering in cyanobacteria." Appl Environ Microbiol. (1999), 65 (2):523-8.

(Continued)

*Primary Examiner*—Ganapathirama Raghu
(74) *Attorney, Agent, or Firm*—Edwin S. Flores; Daniel J. Chalker; Chalker Flores, LLP

(57) ABSTRACT

The present invention includes compositions and methods for making and using an isolated cyanobacterium that includes a portion of an exogenous bacterial cellulose operon sufficient to express bacterial cellulose, whereby the cyanobacterium produces extracellular glucose. The compositions and methods of the present invention may be used as a new global crop for the manufacture of cellulose, $CO_2$ fixation, for the production of alternative sources of conventional cellulose as well as a biofuel and precursors thereof.

6 Claims, 3 Drawing Sheets

OTHER PUBLICATIONS

Eriksson, I.S., et al., "SALSA: a simulation tool to assess ecological sustainability of agricultural production." Ambio. 34 (4-5):388-92, Jun. 2005.

Galperin, M.Y., et al., "Novel domains of the prokaryotic two-component signal transduction systems." FEMS Microbiol Lett. (2001), 203(1):11-21.

Helenius, G., et al., "In vivo biocompatibility of bacterial cellulose." Biomed Mater Res A. (2006), 76(2):431-8.

Kim, S.G., et al., "Harvesting of Spirulina platensis by cellular flotation and growth stage determination." Lett Appl Microbiol. (2005), 40(3):190-4.

Klemm, D., et al., "Cellulose: Fascinating Biopolymer and Sustainable Raw Material." Angew Chem Int. (2005), 44:3358-3393.

Kondo, T., et al., "'Nematic ordered cellulose': a concept of glucan chain association." Biomacromolecules. (2001), 2 (4):1324-30.

Lynd, L.R., et al., "Microbial cellulose utilization: fundamentals and biotechnology." Microbiol Mol Biol Rev. (2002), 66 (3):506-577.

Moreno, J., et al, "Outdoor cultivation of a nitrogen-fixing marine cyanobacterium," Anabaena sp. ATCC 33047. Biomol Eng. (2003), 20(4-6):191-7.

Nair, U., et al., "Functional elements of the strong psbAI promoter of Synechococcus elongatus PCC 7942." J Bacteriol. (2000), 83(5):1740-7.

Nobles, D.R., et al., "Cellulose in cyanobacteria. Origin of vascular plant cellulose synthase?" Plant Physiol. (2001), 127(2):529-42.

Peng, L., et al., "The experimental herbicide CGA 325'615 inhibits synthesis of crystalline cellulose and causes accumulation of non-crystalline beta-1,4-glucan associated with CesA protein." Plant Physiol. (2001), 126(3):981-92.

Peng, L, et al., "Sitosterol-beta-glucoside as primer for cellulose synthesis in plants." Science. (2002), 295(5552): 147-50.

Römling, U., et al., "C-di-GMP: the dawning of a novel bacterial signaling system." Mol Microbiol. (2005), 57 (3):629-639.

Sakamoto, T., et al., "Growth at low temperature causes nitrogen limitation in the Cyanobacterium Synechococcus sp. PCC 7002." Arch Microbiol. (1998), 169 : 10-19.

Saxena, I.M., et al., "Characterization of genes in the cellulose synthesizing operon (acs operon) of Acetobacter xylinum: implications for cellulose crystallization." J Bacteriol (1994), 176:5735-5752.

Shah, J., et al., "Towards electronic paper displays made form microbial cellulose." Appl Microbiol Biotechnol. (2005), 66:352-355.

Shevchuk, N. A., et al., "Construction of long DNA molecules using long PCR-based fusion of several fragments simultaneously." Nuc Acids Res. (2004), 32(2):e19.

Tabuchi, M., et al., "Bio-sensing on a chip with compact discs and nanofibers." Lab Chip. (2005), 5(12):1412-1415.

Zogaj, X., et al., "The multicellular morphotypes of Salmonella typhimurium and Escherichia coli produce cellulose as the second component of the extracellular matrix." Mol Microbiol. (2001), 39:1452-63.

Ladas, N. P., et al., "Cell Turgor: A Critical Factor for the Proliferation of Cyanobacteria at Unfavorable Salinity," Photosynthesis Research (2000), 65:155-164.

Kallas, T., et al., "Internal pH and ATP-ADP Pools in the Cyanobacterium Synechococcus sp. During Exposure to Growth-Inhibiting Low pH," Journal of Bacteriology (1982), 149:229-236.

http://www/pasteur.fr/recherche/banques/PCC/focs/pcc7002.htm, accessed Nov. 17, 2008.

Roberts, M., "Organic Compatible Solutes of Halotolerant and Halophilic Microorganisms," Saline Systems (2005), http://www.salinesystems.org/content/1/1/5.

Tabita, F. R., et al., "Carbon Dioxide Assimilation in Cyanobacteria : Regulation of Ribulose 1,5-Bisphosphate Carboxylase," Journal of Bacteriology (1979), 140:452-458.

Whisstock, et al., "Prediction of Protein Function from Protein Sequence," Q Rev Biophysics (2003), 36:307-340.

* cited by examiner

PRODUCTION AND SECRETION OF GLUCOSE IN PHOTOSYNTHETIC PROKARYOTES (CYANOBACTERIA)

CROSS-REFERENCE TO RELATED APPLICATIONS

This application claims priority to U.S. Provisional Patent Application Ser. No. 60/849,363, filed Oct. 4, 2006, the entire contents of which are incorporated herein by reference.

STATEMENT OF FEDERALLY FUNDED RESEARCH

This invention was made with U.S. Government support under Contract No. DE-FG02-03R15396 awarded by the Department of Energy. The government has certain rights in this invention.

TECHNICAL FIELD OF THE INVENTION

The present invention relates in general to the field of exogenous gene expression, and more particularly, to the expression of exogenous cellulose synthase genes in cyanobacteria which result in the production and extracellular production of glucose.

BACKGROUND OF THE INVENTION

Without limiting the scope of the invention, its background is described in connection with cellulose production.

Cellulose biosynthesis has a significant impact on the environment and human economy. The photosynthetic conversion of $CO_2$ to biomass is primarily accomplished through the creation of the cellulosic cell walls of plants and algae (Lynd et al., 2002). With approximately $10^{11}$ tons of cellulose created and destroyed annually (Hess et al., 1928), this process ameliorates the adverse effects of increased production of greenhouse gasses by acting as a sink for $CO_2$ (Brown, 2004). Although cellulose is synthesized by bacteria, protists, and many algae; the vast majority of commercial cellulose is harvested from plants.

Timber and cotton are the primary sources of raw cellulose for a number of diverse applications including textiles, paper, construction materials, and cardboard, as well as cellulose derived products such as rayon, cellophane, coatings, laminates, and optical films. Wood pulp from timber is the most important source of cellulose for paper and cardboard. However, extensive processing is necessary to separate cellulose from other cell wall constituents (Klemm et al. 2005; Brown, 2004). Both the chemicals utilized to extract cellulose from associated lignin and hemicelluloses from wood pulp and the waste products generated by this process pose serious environmental risks and disposal problems (Bajpai, 2004). Additionally, the cultivation of other cellulose sources, such as cotton, entails the extensive use of large tracts of arable land, fertilizers and pesticides (both of which require petroleum for their manufacture), and dwindling fresh water supplies for irrigation.

SUMMARY OF THE INVENTION

More particularly, the present invention includes compositions, methods, systems and kits for the production of microbial cellulose using cyanobacteria that include a portion of an exogenous cellulose operon sufficient to express bacterial cellulose. Examples of cyanobacteria for use with the present invention include those that are photosynthetic, nitrogen-fixing, capable of growing in brine, facultative heterotrophs, chemoautotrophic, and combinations thereof.

In one embodiment, the present invention includes compositions and methods for isolated cyanobacteria that include a portion of an exogenous bacterial cellulose operon sufficient to express bacterial cellulose, whereby the cyanobacterium is capable of the extracellular production of glucose. In one aspect, the cyanobacterium is further defined as producing extracellular glucose in the form of monosaccharides, disaccharides, oligosaccharides or polysaccharides from photosynthesis. In another aspect, the cyanobacterium is further defined as making monosaccharides, disaccharides, oligosaccharides or polysaccharides that comprise glucose and cellulose. Examples of cyanobacteria for use with the present invention include *Synechococcus* sp. PCC 7002, *Synechococcus leopoliensis* strain UTCC100, *Agmenellum quadruplicatum* UTEX B2268, and *Synechococcus* sp. ATCC 27264. Furthermore, the glucose, the cyanobacterial extracellular sheath or both are further processed as a renewable feedstock for biofuel production. In one aspect, the cyanobacterium can fix $CO_2$ while producing cellulose and reducing atmospheric $CO_2$ that are quantified as carbon credits which are then sold in the open market, e.g., a carbon credit market. In one aspect, the cyanobacteria increase the extracellular production of monosaccharides, disaccharides, oligosaccharides or polysaccharides upon exposure to acidic conditions.

Another embodiment of the present invention includes an isolated cyanobacterium, which includes a *Synechococcus* sp., with a portion of an exogenous bacterial cellulose operon sufficient to express bacterial cellulose, whereby the cyanobacterium is capable of secreting monosaccharides, disaccharides, oligosaccharides or polysaccharides that include glucose. In one aspect, the cyanobacterium is further defined as producing extracellular glucose in the form of monosaccharides, disaccharides, oligosaccharides or polysaccharides from photosynthesis. In another aspect, the cyanobacterium is further defined as making monosaccharides, disaccharides, oligosaccharides or polysaccharides that comprise glucose and cellulose. Example of cyanobacteria include *Synechococcus* sp. PCC 7002, *Synechococcus leopoliensis* strain UTCC100, *Agmenellum quadruplicatum* UTEX B2268, and *Synechococcus* sp. ATCC 27264. The cellulose, the cyanobacterial extracellular sheath or both are further processed as a renewable feedstock for biofuel production.

Another method of the present invention includes producing a photobiomass that may include monosaccharides, disaccharides, oligosaccharides or polysaccharides that include glucose, by modifying a cyanobacterium with a portion of an exogenous bacterial cellulose operon sufficient to express and produce extracellular glucose; growing the cyanobacterium under conditions that promote extracellular glucose production; and exposing the cyanobacteria to an acidic condition, wherein the acid increases glucose secretion. The method may further include the step of processing the glucose into ethanol. For example, the glucose is used as a renewable feedstock for biofuel production, to fix $CO_2$ and thus atmospheric $CO_2$ or even as a renewable feedstock for animals.

Another embodiment of the present invention includes a method of fixing carbon by growing a cyanobacterium comprising a portion of an exogenous bacterial cellulose operon sufficient to make cellulose and produce extracellular glucose in a $CO_2$-containing growth medium; generating glucose with said cyanobacterium, wherein $CO_2$ is fixed into glucose at a level higher than an unmodified cyanobacterium; and calculating the amount of $CO_2$ fixed into the glucose to equate to one or more carbon credit units. For example, at least one other carbon is fixed into glucose and the at least one other carbon's is equated to carbon credit units that is included in the calculation.

In another embodiment of the present invention includes an isolated cyanobacterium that expresses a portion of an exogenous bacterial cellulose operon sufficient to express bacterial cellulose, whereby the cyanobacterium is capable of producing extracellular monosaccharides, disaccharides, oligosaccharides or polysaccharides.

A vector for expression of a portion of the cellulose operon sufficient to express bacterial cellulose operon that includes a microbial cellulose operon, e.g., the acsAB gene operon, under the control of a promoter that expresses the genes in the operon in cyanobacteria. The skilled artisan will recognize that the vector may combine portions of the operons of bacterial, algal, fungal and plant cellulose operons to maximize production and/or change the characteristics of the cellulose and may be transfer and/or expression vector.

The compositions and methods of the present invention also include the use of the cyanobacteria-produced cellulose, which has a lower crystallinity than wild-type bacterial cellulose and allows for easier degradation to glucose for use in subsequent fermentation to ethanol. One distinct advantage of the present invention is that it permits very large scale production of cellulose in areas that would otherwise not be available for cellulose production (e.g., areas with little or no rainfall) while at the same time producing cellulose with less toxic byproducts. The cellulose of the present invention has a lower crystallinity than wild-type bacterial cellulose and the lower crystallinity cellulose is degraded with less energy into glucose than wild-type cellulose and is further converted into ethanol.

The system for the manufacture of bacterial cellulose may further include growing an exogenous cellulose expressing cyanobacterium adapted for growth in a hypersaline environment, such that the cyanobacterium does not grow in fresh water or the salinity of sea water. The growth of the cyanobacteria in a hypersaline environment may be used as way to limit the potential for unplanned growth of the cyanobacteria outside controlled areas. In one example, the cellulose expressing cyanobacteria of the present invention may be grown in brine ponds obtained from subterranean formation, such a gas and oil fields. Examples of cyanobacteria for use with the system include those that are photosynthetic, nitrogen-fixing, capable of growing in brine, facultative heterotrophs, chemoautotrophic, and combinations thereof. As with the previous embodiments of the present invention, the cellulose genes may even obtained from mosses such as Physcomitriella, algae, ferns, vascular plants, tunicates, gymnosperms, angiosperms, cotton, switchgrass and combinations thereof. The skilled artisan will recognize that it is possible to combine portions of the operons of bacterial with algal, fungal and plant cellulose genes to maximize production and/or change the characteristics of the cellulose.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
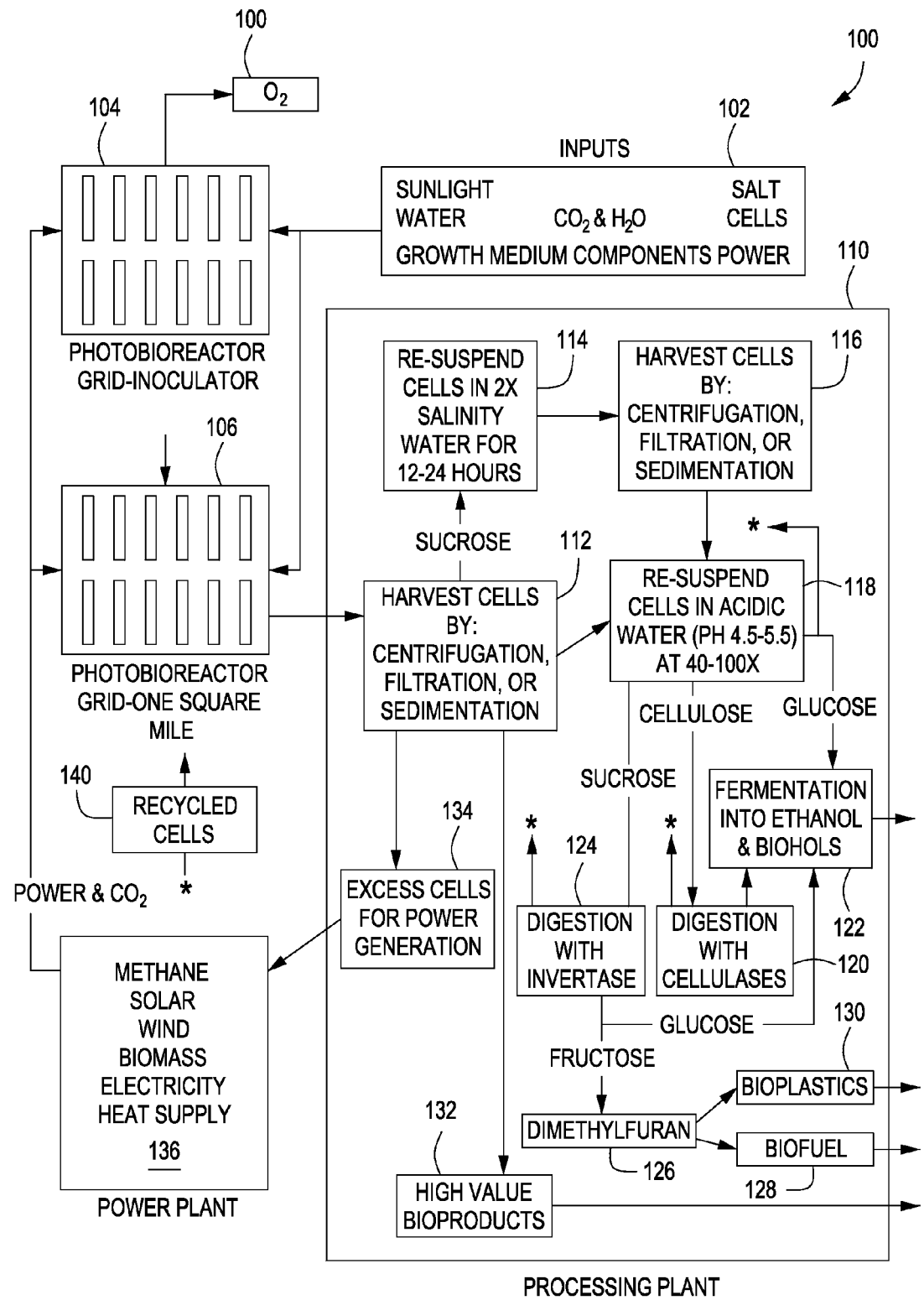
FIG. 1 shows a diagram of a production plant that may be used to produce, isolate and process the saccharides produced using the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term, "cellulose" and "cellulose substrate" include not only bacterial cellulose, but also native cellulose from any source such trees, cotton, any vascular plant (angiosperms and gymnosperms), any non-vascular plant such as algae, mosses, liverworts, any animal that synthesizes cellulose (such as tunicates or sea squirts), any prokaryotic organism (such as cyanobacteria, purple bacteria, archaebacteria, etc. A complete list and classification is available from the present inventors at: http://128.83.195.51/cen/library/tree/cel.htm. As the inventors' list shows, the cellulose may be from an organism that has one or more cellulose synthase genes present. Furthermore, cellulose also includes any derivatized form of cellulose such as cellulose nitrate, acetate, carboxymethylcellulose, etc. Cellulose also includes any form of native crystalline cellulose, which includes not only the native crystalline form (called cellulose I, in its alpha and beta sub allomorphs, all ratios, whether pure alpha or pure beta). Cellulose for use with the present invention also includes all processed crystalline celluloses, which deviates from the native form of cellulose I, such as cellulose II (which is a precipitated crystalline allomorph that is thermodynamically more stable than cellulose I). Cellulose includes all variations of molecular weights ranging from the lowest (oligosaccharides, 2-50 glucan monomers with a B-1,4 linkage), low molecular weight celluloses with a degree of polymerization (dp), which is the number of glucose molecules in the chain, of 50 to several hundred, on up to the highest dp celluloses known (e.g., 15,000 from some *Acetobacter* strains, to 25,000 from some algae). The present invention may also use all variations of non crystalline cellulose, including but not limited to, nematic ordered cellulose (NOC).

As used herein, the terms "continuous method" or "continuous feed method" refer to a fermentation method that includes continuous nutrient feed, substrate feed, cell production in the bioreactor, cell removal (or purge) from the bioreactor, and product removal. Such continuous feeds, removals or cell production may occur in the same or in different streams. A continuous process results in the achievement of a steady state within the bioreactor. As used herein, the term "steady state" refers to a system and process in which all of these measurable variables (i.e., feed rates, substrate and nutrient concentrations maintained in the bioreactor, cell concentration in the bioreactor and cell removal from the bioreactor, product removal from the bioreactor, as well as conditional variables such as temperatures and pressures) are relatively constant over time.

As used herein, the terms "photobioreactor," "photoreactor," or "cyanobioreactor," include a fermentation device in the form of ponds, trenches, pools, grids, dishes or other vessels whether natural or man-made suitable for inoculating the cyanobacteria of the present invention and providing to one or more of the following: sunlight, artificial light, salt, water, $CO_2$, $H_2O$, growth media, stirring and/or pumps, gravity or force fed movement of the growth media. The product of the photobioreactor will be referred to herein as the "photobiomass". The "photobiomass" includes the cyanobacteria, secreted materials and mass formed into, e.g., cellulose or value added products whether intra or extracellular.

As used herein, the terms "bioreactor," "reactor," or "fermentation bioreactor," include a fermentation device that includes of one or more vessels and/or towers or piping arrangement, which includes the Continuous Stirred Tank Reactor (CSTR), Immobilized Cell Reactor (ICR), Trickle Bed Reactor (TBR), Bubble Column, Gas lift Fermenter, Static Mixer, or other device suitable for gas-liquid contact. A fermentation bioreactor for use with the present invention includes a growth reactor which feeds the fermentation broth to a second fermentation bioreactor, in which most products, e.g., alkanols or furans are produced. In some cases, the gaseous byproduct of fermentation, e.g., $CO_2$, can be pumped back into the photobioreactor to recycle the gas and promote the formation of saccharides by photosynthesis. To the extent that heat is generated during the process of recovering the products of the fermentation, etc., the heat can also be used to promote cyanobacterial cell growth and production of saccharides.

As used herein, the term "nutrient medium" refers to conventional cyanobacterial growth media that includes sufficient vitamins, minerals and carbon sources to permit growth and/or photosynthesis of the cellulose producing cyanobacteria of the present invention. Components of a variety of nutrient media suitable to the use of this invention are known and reported in e.g., Cyanobacteria, Volume 167: (Methods in Enzymology) (Hardcover), by John N. Abelson Melvin I. Simon and Alexander N. Glazer (Editors), Academic Press, New York (1988).

As used herein, the term "cell concentration" refers to the dry weight of cyanobacteria per liter of sample. Cell concentration is measured directly or by calibration to a correlation with optical density.

As used herein, the term "saccharide production" refers to the amount of mono-, di-, oligo or polysaccharides produced by the modified-cyanobacteria of the present invention that produce saccharides by fixing carbon such as $CO_2$ by photosynthesis into the saccharides. One distinct advantage of the present invention is that the cyanobacteria do not produce lignin along with the production of the cellulose and other saccharides that can be used as a feed-stock for fermentation and other bioreactors that convert the saccharides into, e.g., ethanol or other synfuels.

In operation, the present invention may use any of a variety of known fermentation process steps, compositions and methods for converting the saccharides into useful products, e.g., lignin-free cellulose, alkanols (alkyl alcohols), furans and the like. One non-limiting example of a process for producing ethanol by fermentation is a process that permits the simultaneous saccharification and fermentation step by placing the saccharide source at a temperature of above 34° C. in the presence of a glucoamylase and a thermo-tolerant yeast.

In this example, the following main process stages may be included saccharification (if necessary), fermentation and distillation. One particular advantage of the present invention is that it eliminates a variety of processing steps, including, milling, bulk-fiber separations, recovery or treatments for the control or elimination of lignin, water removal, distillation and burning of unwanted byproducts. Any of the process steps of alcohol production may be performed batchwise, as part of a continuous flow process or combinations thereof.

Saccharification. To produce mono- and di-saccharides from the lignin-free cellulose of the present invention the cellulose can be metabolized by cellulases that provide the yeast with simple saccharides. This "saccharification" step include the chemical or enzymatic hydrolysis of long-chain oligo and polysaccharides by enzymes such as cellulase, glucoamylases, alpha-glucosidase, alkaline, acid and/or thermophilic alpha-amylases and if necessary phytases.

Depending on the length of the polysaccharides, enzymatic activity, amount of enzyme and the conditions for saccharification, this step may last up to 72 hours. Depending on the feedstock, the skilled artisan will recognize that saccharification and fermentation may be combined in a simultaneous saccharification and fermentation step.

Fermentation. Any of a wide-variety of known microorganism may be used for the fermentation, fungal or bacterial. For example, yeast may be added to the feedstock and the fermentation is ongoing until the desired amount of ethanol is produced; this may, e.g., be for 24-96 hours, such as 35-60 hours. The temperature and pH during fermentation is at a temperature and pH suitable for the microorganism in question, such as, e.g., in the range about 32-38° C., e.g. about 34° C., above 34° C., at least 34.5° C., or even at least 35° C., and at a pH in the range of, e.g., about pH 3-6, or even about pH 4-5. The skilled artisan will recognize that certain buffers may be added to the fermentation reaction to control the pH and that the pH will vary over time.

The use of a feed stock that includes monosaccharides, in addition to the use of thermostable acid alpha-amylases or a thermostable maltogenic acid alpha-amylases and invertases in the saccharification step may make it possible to improve the fermentation step. When using a feedstock that includes large amounts of monosaccharides such as glucose and sucrose, for the production of ethanol it may be possible to reduce or eliminate the need for the addition of glucoamylases in the fermentation step or prior to the fermentation step.

Distillation. To complete the manufacture of final products from the saccharides made by the cyanobacterial fixation of $CO_2$ of the present invention, the invention may also include recovering the alcohol (e.g., ethanol). In this step, the alcohol may be separated from the fermented material and purified with a purity of up to e.g. about 96 vol. % ethanol can be obtained by the process of the invention.

Several specific enzymes and methods may be used to improve the recovery of energy containing molecules from the present invention. The enzymes improve the saccharification and fermentation steps by selecting their most efficient activity as part of the processing of the products of the saccharide producing modified cyanobacteria of the present invention.

In one example, a thermo tolerant cellulase may be introduced into the reactor to convert cellulose produced by the cyanobacteria of the present invention into monosaccharides, which will mostly be glucose. Examples of thermophilic cellulases are known in the art as taught in, e.g., U.S. Patent Application No 20030104522 filed by Ding, et al. that teach a thermal tolerant cellulase from *Acidothermus cellulolyticus*. Yet another example is taught by U.S. Patent Application No. 20020102699, filed by Wicher, et al., which teaches variant thermostable cellulases, nucleic acids encoding the variants and methods for producing the variants obtained from *Rhodothermus marinus*. The relevant portions of each are incorporated herein by reference.

Acid cellulase may be obtained commercially from manufacturers such as Ideal Chemical Supply Company, Memphis Tenn., USA; Americos Industries Inc., Gujarat, India; Rakuto Kasei House, Yokneam, Israel; or Novozymes, Bagsvaerd, Denmark. For example, the acid cellulase may be provided in dry, liquid or high-active abrasive form, as is commonly used in the denim acid washing industry using techniques known to the skilled artisan. For example, Americos Cellscos 450 AP is a highly concentrated acid cellulase enzyme produced using genetically modified strains of *Trichoderma reesii*. Typically, the acid cellulases function in a pH range or 4.5-5.5.

Microorganisms used for fermentation. One example of a microorganism for use with the present invention is a thermotolerant yeast, e.g., a yeast that when fermenting at 35° C. maintains at least 90% of the ethanol yields and 90% of the ethanol productivity during the first 70 hours of fermentation, as compared to when fermenting at 32° C. under otherwise similar conditions. One example of thermotolerant yeast is a yeast that is capable of producing at least 15% V/V alcohol from a corn mash comprising 34.5% (w/v) solids at 35° C. One such thermo-tolerant yeast is Red Star®/Lesaffre Ethanol Red (commercially available from Red Star®/Lesaffre, USA, Product No. 42138). The ethanol obtained using any known method for fermenting saccharides (mono, di-, oligo or poly) may be used as, e.g., fuel ethanol, drinking ethanol, potable neutral spirits, industrial ethanol or even fuel additives.

Examples of ethanol fermentation from sugars are well-known in the art as taught by, e.g., U.S. Pat. No. 4,224,410 to Pemberton, et al. for a method for ethanol fermentation in which fermentation of glucose and simultaneous-saccharification fermentation of cellulose using cellulose and a yeast are improved by utilization of the yeast *Candida brassicae*, ATCC 32196; U.S. Pat. No. 4,310,629 to Muller, et al., that teaches a continuous fermentation process for producing ethanol in which continuous fermentation of sugar to ethanol in a series of fermentation vessels featuring yeast recycle which is independent of the conditions of fermentation occurring in each vessel is taught; U.S. Pat. No. 4,560,659 to Asturias for ethanol production from fermentation of sugar cane that uses a process for fermentation of sucrose wherein sucrose is extracted from sugar cane, and subjected to stoichiometric conversion into ethanol by yeast; and U.S. Pat. No. 4,840,902 to Lawford for a continuous process for ethanol production by bacterial fermentation using pH control in which a continuous process for the production of ethanol by fermentation of *Zymomonas* spp. is provided. The method of Lawford is carried out by cultivating the organism under substantially steady state, anaerobic conditions and under conditions in which ethanol production is substantially uncoupled from cell growth by controlling pH in the fermentation medium between a pH of about 3.8 and a pH less than 4.5; and K A Jacques, T P Lyons & D R Kelsall (Eds) (2003), The Alcohol Textbook; $4^{TH}$ Edition, Nottingham Press; 2003. The relevant portions of each of which are incorporated herein by reference.

One of ordinary skill in the art would recognize that the quantity of yeast to be contacted with the photobiomass will depend on the quantity of the photobiomass, the secreted portions of the photobiomass and the rate of fermentation desired. The yeasts used are typically brewers' yeasts. Examples of yeast capable of fermenting the photobiomass include, but are not limited to, *Saccharomyces cerevisiae* and *Saccharomyces uvarum*. Besides yeast, genetically altered bacteria know to those of skill in the art to be useful for fermentation can also be used. The fermenting of the phototbiomass is conducted under standard fermenting conditions.

Separating of the ethanol from the fermentation can be achieved by any known method (e.g. distillation). The separation can be performed on either or both the liquid and solid portions of the fermentation solution (e.g., distilling the solid and liquid portions), or the separation can just be performed on the liquid portion of the fermentation solution (e.g., the solid portion is removed prior to distillation). Ethanol isolation can be performed by a batch or continuous process. The separated ethanol, which will generally not be fuel-grade, can be concentrated to fuel grade (e.g., at least 95% ethanol by volume) via additional distillation or other methods known to those of skill in the art (e.g., a second distillation).

The level of ethanol present in the fermentation solution can negatively affect the yeast/bacteria. For example, if 17% by volume or more ethanol is present, then it will likely begin causing the yeast/bacteria to die. As such, ethanol can be separated from the fermentation solution as the ethanol levels (e.g., 12, 13, 14, 15, 16, to 17% by volume (ethanol to water)) that may kill the yeast or bacteria are reached. Ethanol levels can be determined using methods known to those of ordinary skill in the art.

The fermentation reaction can be run multiple times on the photobiomass or portions thereof. For example, once the level of ethanol in the initial fermentation reactor reaches 12-17% by volume, the entire liquid portion of the fermentation solution can be separated from the biomass to isolate the ethanol (e.g., distillation). The "once-fermented" photobiomass can then be contacted with water, additional enzymes and yeast/bacteria for additional fermentations, until the yield of ethanol is undesirably low. Factors that the skilled artisan will use to determine the number of fermentations include: the amount of photobiomass remaining in the vessel; the amount of carbohydrate remaining, the type of yeast or bacteria, the temperature, pH, salt concentration of the media and overall ethanol yield. If any carbohydrates remain, then the remaining photobiomass is removed from the vessel.

Generally, it is desirable to isolate or harvest the yeast/bacteria from the fermentation reaction for recycling. The method of harvesting will depend upon the type of yeast/bacteria. If the yeast/bacteria are top-fermenting, they can be skimmed off the fermentation solution. If the yeast/bacteria are bottom-fermenting, they can be removed from the bottom of the tank.

Often, a by-product of fermentation is carbon dioxide, which is readily recycled into the photobioreactor for fixation into additional saccharides. During the fermentation process, it is expected that about one-half of the decomposed starch will be discharged as carbon dioxide. This carbon dioxide can be collected by methods known to those of skill in the art (e.g., a floating roof type gas holder) and is supplied back into the photobioreactor pool or pools. In colder climates, the heat that may accompany the carbon dioxide will help in the growth of the cyanobacterial pools.

One advantage of the present invention is that it provides a novel $CO_2$ fixation method for the recycling of environmental greenhouse gases. The present invention provides a source of substrate for cellulose production from carbon dioxide that is fixed into sugar by photosynthesis, thereby removing a major barrier limiting large global scale production of cellulose. If the present invention is successful on a large scale, it will sequester $CO_2$ from the air, thus reducing the potential greenhouse gas responsible for global warming. Another benefit of the present invention is that forests and cotton crops, the present sources for cellulose, may not be needed in the future, thus freeing the land to allow regeneration of forests and use of cropland for other needs.

Microbial cellulose stands as a promising possible alternative to traditional plant sources. The a proteobacterium *Acetobacter xylinum* (synonym *Gluconacetobacter xylinum* [Yamada et al., 1997]) is the most prolific of the cellulose producing microbes. The NQ5 strain (Brown and Lin, 1990) is capable of converting 50% of glucose supplied in the medium into an extracellular cellulosic pellicle (R. Malcolm Brown, Jr., personal communication). Although it possesses the same molecular formula as cellulose derived from plant sources, microbial cellulose has a number of distinctive properties that make it attractive for diverse applications. The cellulose synthesized by *A. xylinum* is "spun" into the growth medium as highly crystalline ribbons with exceptional purity, free from the contaminating polysaccharides and lignin found in most plant cell walls (Brown et al., 1976). The resulting membrane or pellicle is composed of cellulose with a high degree of polymerization (2000-8000) and crystallinity (60-90%) (Klemm, et al., 2005). Contaminating cells are easily removed, and relatively little processing is required to prepare membranes for use. In its never-dried state, the membrane displays exceptional strength and is highly absorbent, holding hundreds of times its weight in water (White and Brown, 1989). *A. xylinum* cellulose is therefore, well suited as a reinforcing agent for paper and diverse specialty products (Shah and Brown, 2005; Czaja et al., 2006; Tabuchi et al., 2005; Helenius et al., 2006).

The acsAB genes from the cellulose synthase operon of or the gram negative bacterium, *Acetobacter xylinum* (=*Gluconacetobacter xylinus*) under control of a lac promoter have been integrated into the chromosome of a photosynthetic cyanobacterium, *Synechococcus leopoliensis*. UTCC 100. The presence of the genes in the chromosome has been confirmed by PCR. Preliminary data from Western analysis, light microscopy, and growth characteristics suggests functional expression of these genes in *Synechococcus*. Cyanobacteria expressing exogenous cellulose synthase genes will be used for the efficient and inexpensive production of bacterial cellulose.

Despite it superior quality, the use of microbial cellulose as a primary constituent for large scale use in common applications such as the production of construction materials, paper, or cardboard has not been economically feasible. The root cause for the expense of microbial cellulose production is the heterotrophic nature of *A. xylinum*. Bacterial cultures must be supplied with glucose, sucrose, fructose, glycerol, or other carbon sources produced by the cultivation of plants. Increased distance from the primary energy source is inherently less efficient and inevitably leads to increased cost of production when compared with phototrophic sources. Therefore, while the unique properties of *A. xylinum* cellulose make it indispensable for a number of value added products, it is not well suited for the more general applications that constitute the vast majority of cellulose utilization (Brown, 2004; White and Brown, 1989), e.g., to replace the use of forests for the production of paper and to provide substrates for the production of biofuels based on ethanol using photosynthesis as the source of energy for $CO_2$ fixation. As such, the present invention provides compositions and methods for the manufacture of a new global crop that may be used for energy production and removal of the greenhouse gas $CO_2$ using an environmentally acceptable natural process that requires little or no energy input for manufacture.

Currently, bacterial cellulose is produced by *A. xylinum*, a heterotrophic a proteobacterium. The fact that the precursor of cellulose, namely glucose, needs to be supplied, presents a bottleneck in large scale production of microbial cellulose. Present technology would suggest using sugarcane extracts, sucrose, beet sugar, etc., as sources. If the rate of cellulose biosynthesis in cyanobacteria is increased via the expression of exogenous cellulose synthase genes, then the potential for an economical global cellulose crop is possible. Cellulose synthase genes have been stably integrated into the chromosome by recombination but also could be expressed on replicating plasmids.

Unlike *A. xylinum*, cyanobacteria require no fixed carbon source for growth. Additionally, many cyanobacteria are capable of nitrogen fixation, which would eliminate the need for fertilizers necessary for cellulose crops like cotton. Furthermore, many cyanobacteria are halophilic, that is, they can grow in a the range of brackish to hypersaline environments. This feature, in combination with N-fixation, will allow non-arable, sun-drenched areas of the planet to provide the extensive surface areas for the growth and harvest of cellulose made using the compositions and methods of the present invention on a global scale.

Cyanobacterial cellulose can be used in diverse applications where a combination of products is simultaneously made from photosynthesis. Value added products may include pharmaceuticals and/or vaccines, vitamins, industrial chemicals, proteins, pigments, fatty acids and their derivatives (such as polyhydroxybutyrate), acylglycerols (as precursors for biodiesel), as well as other secondary metabolites. These products may be the result of natural cyanobacterial metabolic processes or be induced through genetic engineering. The present invention permits large scale production of cellulose, proteins and other products that may be grown and harvested. In fact, wide application of the cells themselves for glucose and cellulose is encompassed by the present invention. The cellulose producing cyanobacteria of the present invention may be utilized for energy recycling and recovery, that is, the cells may be dried and burned to power downstream processes in a manner similar to the use of bagasse in the sugar cane industries.

The ideal cellulose producing organism would synthesize cellulose of a quality and in the quantities observed in *A. xylinum*, have a photoautotrophic lifestyle, and possess the ability to grow with a minimum use of natural resources in environments unsuitable for agriculture. Cyanobacteria are capable of using low photon flux densities for carbon fixation, withstanding hypersaline environments, tolerating desiccation, and surviving high levels of UV irradiation (Vincent, 2000; Wynn-Williams, 2000). Additionally, many species are diazotrophic (Castenholz and Waterbury, 1989). This combination of exceptional adaptive characteristics has made mass cultivation of cyanobacteria attractive for production of nutritional biomass, fatty acids, bioactive compounds, and polysaccharides (Cogne et al., 2005; Moreno et al., 2003; Kim et al., 2005). Although no species of cyanobacteria are known to synthesize cellulose in large quantities, the development of a number of systems for engineering of cyanobacterial chromosomes may offer a means to a new global crop of cellulose produced by cyanobacteria.

Toward this end, genes that include the cellulose synthase operon of *A. xylinum* NQ5 were integrated into the chromosome of the unicellular cyanobacterium, *Synechococcus leopoliensis* UTCC 100 (synonym *Synechococcus elongatus* PCC 7942). Alternatively, a cyanobacterium for use with the present invention may be a salt-water variety that is diazotrophic. *S. elongatus* has served as a model organism for molecular studies of photosynthesis and circadian rhythms, and has been successfully utilized for transgenic expression (Rixin and Golden, 1993; Nair et al., 2000; Deng and Coleman, 1999; Asada et al., 2000). *S. elongatus* has a rapid growth rate, readily recombines DNA into its chromosome by transformation or conjugation, can act as a host for replicating plasmids, and its physiology, genetics, and biochemistry are well characterized (Golden et al., 1987; Thiel, 1995; Deng and Coleman, 1999). Additionally, a project to sequence the genome of this organism is underway (<genome.jgipsf.org/finished_microbes/synel/synel.home.html>). These characteristics facilitate the transfer and expression of exogenous genes and manipulation of native regulatory components.

Culture Conditions. Genetically modified strains of *Synechococcus* (see Table I for a description of strains) were maintained at 24° C. with 12 hour light/dark cycles using BG11 (Allen, 1968) as the growth medium. Solid media was prepared with 1.5% agar as previously described (Golden, 1988). 50 ml liquid cultures were maintained on a rotary shaker in 250 ml Erlenmeyer flasks. Growth media was supplemented with 7.5 ug/ml chloramphenicol. Cell concentrations of cultures were determined by measuring their optical density at 750 nm ($OD_{750}$).

TABLE 1

Strain Characteristics.

| Strain | Relevant Characteristics |
|---|---|
| NS::cat | *Synechococcus leopoliensis* UTCC 100 strain carrying the chloramphenicol acetyltransferase marker in chromosomal neutral site II. This strain was created using vector pAM1573. |
| NS::abΔc7s | *Synechococcus leopoliensis* UTCC 100 strain carrying acsABΔC from *Gluconacetobacter xylinum* strain NQ5 and the chloramphenicol acetyltransferase marker in chromosomal neutral site II. This strain was created using vector pSAB2. |

Determination of Glucose Concentrations

Preparation of Cultures. 50 ml liquid cultures were inoculated by scraping cells from the surface of agar plates with flame-sterilized spatulas such that the initial $OD_{750}$ was 1.67+/−0.22. Cultures of NS::cat and NS::abΔc7S were grown for 7-14 days under the conditions described above. The $OD_{750}$ of each culture was recorded. Cells from 40 ml aliquots of liquid cultures were collected by centrifugation (10 min, RT, 1,744×g) in an IEC clinical centrifuge. The supernatants were discarded and wet weights of the cell pellets were recorded. Pellets were resuspended in 1 ml of 10 mM Sodium Acetate, pH 5.2. 250 ul aliquots of the cell suspension were transferred to 1.5 ml eppendorf tubes. The tubes were incubated overnight on a rotisserie at 30° C. with constant illumination.

Glucose Assays. After overnight incubation, cells were pelleted by centrifugation (5 min, RT, 14,000 rpm) in a microcentrifuge. The supernatant was carefully pipetted off the cell pellet and retained for the glucose assay. Glucose concentration was measured using the hexokinase, glucose 6-phosphate dehydrogenase enzymatic assay (Sigma G3293). Assays were performed with 50-100 ul of supernatant per reaction following the manufacturer's instructions.

Table 2 demonstrates that the expression of genes from the cellulose synthase operon of *Gluconacetobacter xylinus* strain NQ5 in NS::abΔc7S results in an order of magnitude increase in the production of glucose when compared to NS::cat. Assuming lossless scale-up, the observed extracellular glucose production levels of NS::abΔc7S would translate into approximately 380 gallons of ethanol per acre foot per year. This is comparable to current production levels of corn (400 gallons of ethanol per acre) and is roughly one third of the productivity of switchgrass (1150 gallons per acre per year). However, it is important to note that the glucose being produced by our strain does not require extensive pretreatment nor does it require the application of exogenous cellulose digesting enzymes. Thus, the two most costly steps in the conversion of biomass to ethanol are eliminated. Therefore, even with lower production levels, cyanobacterial glucose may be an economically feasible feedstock for ethanol production.

Table 2. Comparison of glucose production levels. Values representing cell concentrations, cell mass, and glucose production by NS::cat and NS::abΔc7S. Optical densities and wet weights were recorded prior to resuspension in 10 mM Sodium Acetate, pH 5.2. The glucose concentration in mg/ml was measured from aliquots of cell suspensions resulting from the concentration of 40 ml of liquid culture into 1 ml of Sodium Acetate.

TABLE 2

Comparison of glucose production levels.

| Strain | $OD_{750}$ | Wet weight (g) | Glucose (mg/ml) | mg Glucose g wet weight | mg Glucose liter |
|---|---|---|---|---|---|
| NS::cat | 1.65 +/− 0.13 | 0.35 +/− 0.10 | 0.12 +/− 0.06 | 0.17 +/− 0.25 | 1.03 +/− 1.40 |
| NS::abΔc7S | 1.82 +/− 0.19 | 0.41 +/− 0.15 | 1.37 +/− 0.06 | 3.70 +/− 1.55 | 34.32 +/− 1.62 |

Not wanting to be bound by theory, several possible mechanisms leading to the release of free glucose into the external milieu may exist. Glucose may be exuded from cells or released from extracellular polysaccharides by the actions of one or more endogenous secreted glycosyl hydrolases, e.g., Syn_PCC79421400 (see e.g., <maple.1sd.orn1.gov/cgi-bin/JGI_microbial/gene_viewer.cgi?org=syn_PCC7942&chr=21jun05&contig=Contig52 &gene=Syn_pcc79421400>) capable of acting on non-crystalline cellulosic material, Discovery of the mechanism responsible for the observed glucose levels will almost certainly uncover novel biological processes and may provide the means for increased glucose production in this organism.

FIG. 1 shows one example of a photobioreactor system 100 of the present invention. First, inputs 102 for the photobioreactor system may include: sunlight, salt, water, $CO_2$ modified-cyanobacterial cells of the present invention, growth medium components and if necessary a source of power to move the components (e.g., pumps or gravity). Next, the inputs 102 and inoculated into a photobioreactor grid 104 that is used to grow the modified-cyanobacteria in size and number, to test for saccharide production and to reach a sufficiently high enough concentration to inoculate the operating photobioreactor 106. The photobioreactor 106 may be a pool or pool(s), trench or other vessel, indoor or outdoor that is used to grow and harvest a sufficient volume of photobiomass for subsequent processing in, e.g., processing plant 110. In one example, the photobioreactor 106 may be a grid of pools of one square mile (or larger) that may be used in parallel or in series to produce the photobiomass. Depending on the geographical location of the photobioreactor 106, the water may be saltwater or brine obtained from a sea that is gravity fed into the pools. Gravity or pumping may be used, however, gravity has the advantage that it does not require additional energy to move the photobiomass from pool to pool and even into the processing plant. In fact, in certain embodiments the entire system may be gravity fed with the final products gravity fed into underground rivers that return to the sea or ocean.

The processing plant 110 includes a cell harvested 112, which may allows the isolation of the photobiomass by, e.g., centrifugation, filtration, sedimentation, creaming or any other method for separating the photobiomass, the modified-cyanobacterial cells and the liquid. For the isolation of sucrose, the cells may be resuspended in medium with an increased salinity 114 (e.g., 2× the salinity) followed by a second harvesting step 116. The twice-harvested cells are then resuspended under acidic conditions (e.g., pH 4.5-5.5) at 40 to 100× the concentration and the sucrose is secreted by the modified-cyanobacteria. If glucose is preferred, the once harvested cells are resuspended under acidic conditions 118 and glucose is secreted. In addition, whether sucrose or glucose is secreted, cellulose is also harvested from the modified-cyanobacteria, which may be further digested by cellulases 120. Glucose and digested cellulose can then be fermented into ethanol or other alkanols.

If sucrose is secreted and obtained, then the sucrose can be converted into dimethylfuran and glucose by invertase 124. The methylfuran 12 can then be used for bioplastic 130 or biofuel 128 production. Glucose that is obtained after the invertase reaction 124 can then be directed back into the fermentation reactions.

In addition to the production of ethanol, bioplastics and other biofuels, the harvested cells can he used for the production of other high value bioproducts, e.g., by further modifying the microbial cellulose-producing cyanobacteria to make other bioproducts, e.g., pharmaceuticals and/or vaccines, vitamins, industrial chemicals, proteins, pigments, fatty acids and their derivatives (such as polyhydroxybutyrate), acylglycerols (as precursors for biodiesel), as well as other secondary metabolites. After each of these steps, the modified-cyanobacteria can then be recycled into the photobioreactors for additional carbon fixation. Furthermore, the products of the processing plant 110 can also be combined with other power sources, e.g., solar, methane, wind, etc., to generate electricity and heat (in addition to recycling any $CO_2$ released in the processing plant 110), to power the inoculation pool 104 and the photobioreactor 106.

Figure 2:
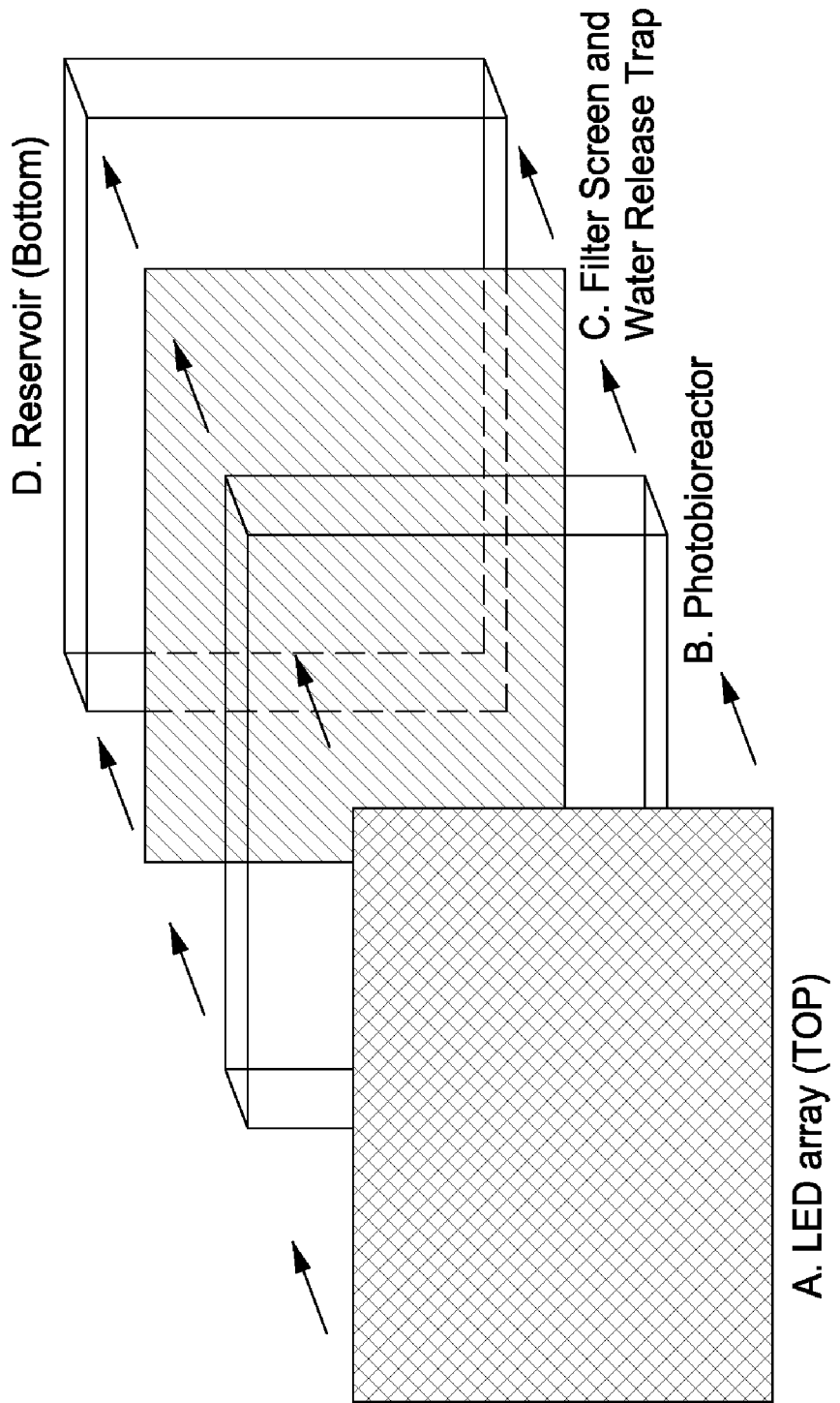
FIG. 2 shows photobioreactor design for in situ harvest of cyanobacterial saccharides.

FIG. 2 shows a photobioreactor design for in situ harvest of cyanobacterial saccharides. The photobioreactor complex can be located indoors or underground. Part A An LED array powered by photovoltaic cells, provides mono or polychromatic light at a pulsed frequencies corresponding to the rate limiting steps of photosynthesis for maximized photosynthetic productivity Part B is a transparent photobioreactor acting as a growth vessel for cyanobacterial cells. The horizontal orientation of the photobioreactor allows for efficient separation of cells from culture medium by use of gravity and air pressure. Part C is a filter screen combined with a water release trap will separate cells from the culture medium. The filter screen will have pore sizes capable of retaining cyanobacterial cells while allowing culture medium to flow into the reservoir. The transfer will be facilitated by gravity and air pressure generated by closing the gas outlet of the photobioreactor. The reservoir, located beneath the photobioreactor, will act to retain culture medium during harvest of saccharides. After harvest, culture medium will be returned to the photobioreactor from the reservoir via pump.

Figure 3:
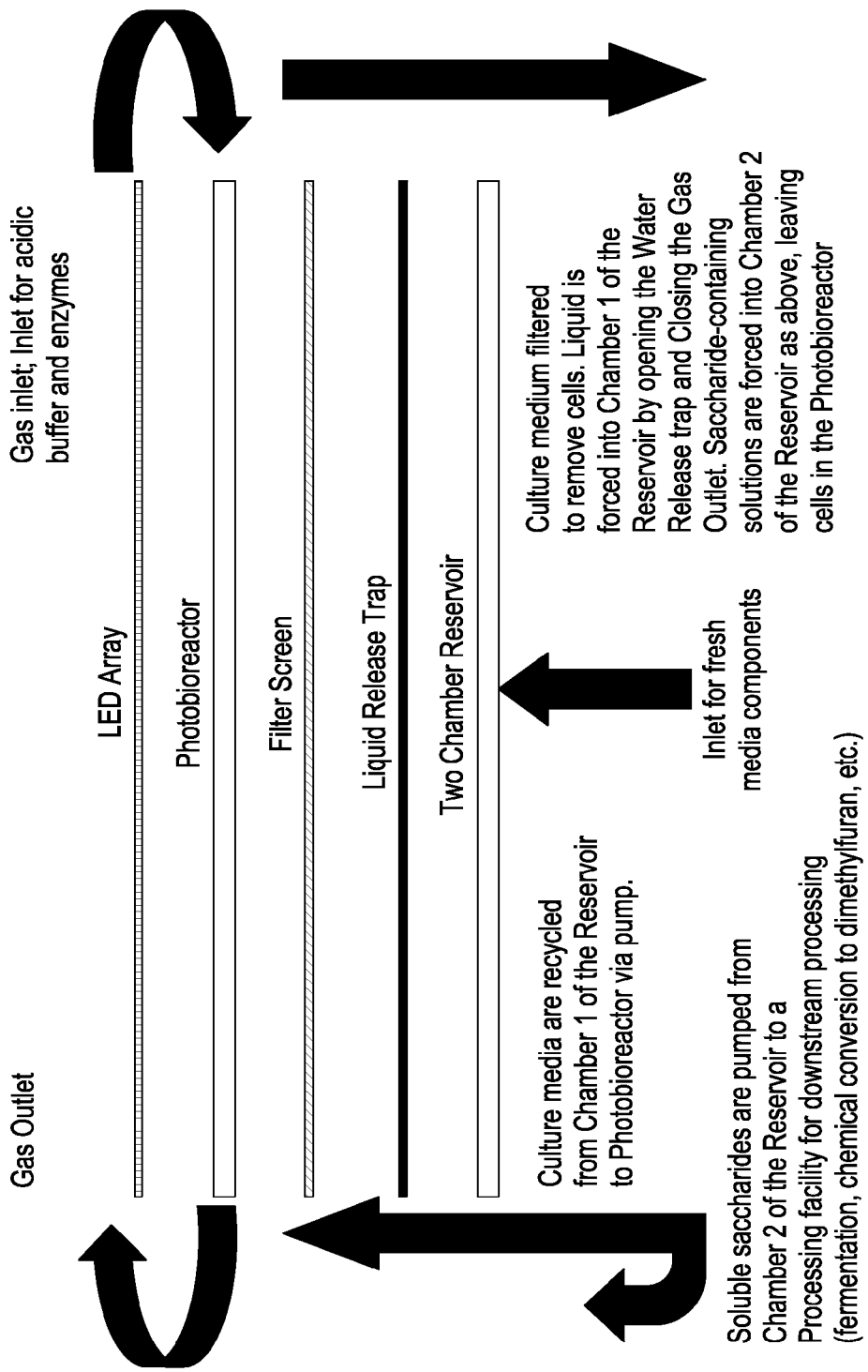
FIG. 3 is a side view of a photobioreactor complex design for in situ harvest of cyanobacterial saccharides.

FIG. 3 shows the operation of a photobioreactor complex design for in situ harvest of cyanobacterial saccharides. The LED array, located on top of the photobioreactor complex will supply pulsed mono or polychromatic light for maximum photosynthetic conversion efficiency. Air flow ($CO_2$, $N_2$, or ambient air) delivered by the gas inlet during growth periods will serve to deliver carbon and/or nitrogen sources for fixation and created turbulence for maintaining cell suspension. A gas outlet will facilitate the release of waste gasses ($O_2$ and $H_2$) that are potentially detrimental to the cyanobacterial growth and relieve excess air pressure from the system during growth phases. Removal of culture media for harvesting of saccharides will be facilitated by the opening of the liquid release trap coupled with closing the gas outlet. The increase in air pressure, combined with gravity, will force the culture medium through the filter which will retain cyanobacterial cells. Cyanobacterial cells can then be resuspended in specific buffer or media designed for cellulose digestion or the direct secretion of saccharides. The saccharide-containing solutions will be drained to chamber 2 of the liquid release trap by the same method described for growth media above. Soluble saccharides will be pumped from chamber 2 of the reservoir to central processing units for downstream conversion processes (e.g., fermentation, chemical conversion to dimethylfuran, etc.). Cells will be resuspended by closing the water release trap and pumping culture medium which has been recombined with fresh media components (e.g., nitrates, phosphates, etc.) from chamber 1 of the reservoir.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

Allen M. (1968). Simple conditions for growth of unicellular blue green algae on plates. J Phycol 4: 1-4.

Golden S S, Brusslan J, Haselkorn R. (1988). Mutagenesis of cyanobacteria by classical and gene-transfer-based methods. In Packer L and Glazer A N (eds) Methods in Enzymology ed. Vol. 167 pp 714-727. Academic Press, Inc. New York.

Nobles D R, Romanovicz D K, Brown R M Jr. (2001). Cellulose in cyanobacteria. Origin of vascular plant cellulose synthase? Plant Physiol. 127 (2):529-42.

Roberts E. (1991). Biosynthesis of Cellulose II and Related Carbohydrates PhD thesis. The University of Texas at Austin, Austin.

Roelofsen P A. (1959). The plant cell wall constituents. In: The Plant Cell Wall. Gebrüder Borntraeger (ed). Felengraff and Co. Berlin. pp 1-33.

Sakamoto T and Bryant D A. (1998). Growth at low temperature causes nitrogen limitation in the cyanobacterium *Synechococcus* sp. PCC 7002. Arch Microbiol. 169: 10-19

Saxena I M, Kudlicka K, Okuda K, Brown R M Jr. (1994) Characterization of genes in the cellulose synthesizing operon (acs operon) of *Acetobacter xylinum*: implications for cellulose crystallization. J Bacteriol 176: 5735-5752.

Stevens S E Jr, Patterson C O P, Myers J. (1973). The production of hydrogen peroxide by blue-green algae: a survey. J. Phycol. 9:427-430.

Tel-Or E, Spath S, Packer L, and Mehlhorn R J. (1986). Carbon-13 NMR Studies of Salt Shock-Induced Carbohydrate Turnover in the Marine Cyanobacterium *Agmenellum quadruplicatum*. Plant Physiol. 82: 646-652.

Updegraff D M. (1969). Semimicro determination of cellulose in biological material. Anal Biochem. 32 (3):420-424.

What is claimed is:

1. An isolated *Synechococcus leopoliensis* strain UTCC100 cyanobacterium comprising an exogenous bacterial cellulose operon from *Acetobacter xylinum* NQ5 comprising the acsAB operon sufficient to express bacterial cellulose, wherein the cyanobacterium is capable of secreting extracellular monosaccharides, disaccharides, oligosaccharides or polysaccharides.

2. The cyanobacterium of claim 1, wherein the cyanobacteria is further defined as producing extracellular glucose and cellulose from photosynthesis.

3. The cyanobacterium of claim 1, wherein the cyanobacteria is further defined as making polysaccharides that comprise glucose.

4. The cyanobacterium of claim 1, wherein the cyanobacterium can fix $CO_2$ while producing cellulose and reducing atmospheric $CO_2$.

5. The cyanobacterium of claim 1, wherein the cyanobacterium increases the extracellular production of monosaccharides, disaccharides, oligosaccharides or polysaccharides upon exposure to acidic conditions.

6. The cyanobacterium of claim 1, wherein extracellular glucose is exuded from cells or released from extracellular polysaccharides by the actions of one or more endogenous secreted glycosyl hydrolases.

* * * * *